United States Patent [19]

Cohnen et al.

[11] Patent Number: 4,801,590

[45] Date of Patent: Jan. 31, 1989

[54] PYRIDO(1,8)NAPHTHYRIDINONES, AND THEIR USE AS PHARMACEUTICALS

[75] Inventors: Erich Cohnen, Jork; Thomas Beuttler; Eva Hofferber, both of Hamburg; Wolfgang Stenzel, Reibek, all of Fed. Rep. of Germany

[73] Assignee: Beiersdorf AG, Hamburg, Fed. Rep. of Germany

[21] Appl. No.: 65,540

[22] Filed: Jun. 23, 1987

[30] Foreign Application Priority Data

Jul. 12, 1986 [DE] Fed. Rep. of Germany ....... 3623533

[51] Int. Cl.[4] .................. A61K 31/435; C07D 471/04
[52] U.S. Cl. .................... 514/293; 514/253; 514/232.5; 514/232.8; 546/82; 544/126; 544/361
[58] Field of Search .................. 546/82; 514/293, 253, 514/237, 227, 239; 544/126, 361

[56] References Cited

FOREIGN PATENT DOCUMENTS 0167045 1/1986 European Pat. Off. ............ 544/126
3423003 1/1986 Fed. Rep. of Germany ........ 546/82

*Primary Examiner*—Mary C. Lee
*Assistant Examiner*—J. Richter
*Attorney, Agent, or Firm*—Sprung Horn Kramer & Woods

[57] ABSTRACT

Pyrido[1,8]naphthyridinones of the general formula I

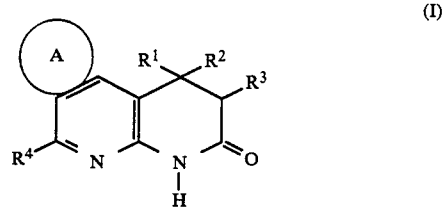

(I)

in which $R^1$ denotes hydrogen, a straight-chain or branched alkyl group having 1 to 6 carbon atoms, the phenyl group or a substituted phenyl group, a cycloalkyl group, a carboxyl group, an alkoxycarbonyl group, a carboxamide group or a cyano group, $R^2$ denotes hydrogen or a straight-chain or branched alkyl group having 1 to 4 carbon atoms, $R^3$ denotes hydrogen, a straight-chain or branched alkyl group having 1 to 4 carbon atoms, a carboxyl group, an alkoxycarbonyl group, a carboxamide group or a cyano group, $R^4$ denotes hydrogen, halogen, the cyano group, the hydroxyl group, a carboxamide group, an alkylthio group or an alkoxy group, in each case having 1 to 6 carbon atoms, which may in each case optionally be substituted by substituted amino groups, furthermore denotes an aryloxy group, an amino group or a substituted amino group, a pyrrolidino, piperidino, hydrazino, morpholino, piperazine or substituted piperazino group, where the alkyl radicals may in each case be straight-chain or branched, and A denotes a pyridine ring, where ring A may also be present in partially hydrogenated form, and the tautomeric forms thereof, and the salts and acid-addition salts thereof, have positive inotropic and vasodilatory properties and can be used as medicaments for the treatment of heart insufficiency, angina pectoris and hypertonia.

8 Claims, No Drawings

PYRIDO(1,8)NAPHTHYRIDINONES, AND THEIR USE AS PHARMACEUTICALS

The invention relates to new pyrido[1,8]naphthyridinones of the general formula I

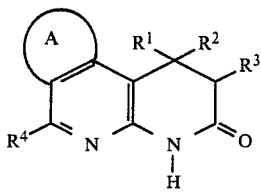

(I)

in which
R$^1$ denotes hydrogen, a straight-chain or branched alkyl group having 1 to 6 carbon atoms, the phenyl group or a substituted phenyl group, a cycloalkyl group, a carboxyl group, an alkoxycarbonyl group, a carboxamide group or cyano group,
R$^2$ denotes hydrogen or a straight-chain or branched alkyl group having 1 to 4 carbon atoms,
R$^3$ denotes hydrogen, a straight-chain or branched alkyl group having 1 to 4 carbon atoms, a carboxyl group, an alkoxycarbonyl group, a carboxamide group or a cyano group,
R$^4$ denotes hydrogen, halogen, the cyano group, the hydroxyl group, a carboxamide group, an alkylthio group or an alkoxy group, in each case having 1 to 6 carbon atoms, which may in each case be optionally substituted by substituted amino groups, furthermore denotes an aryloxy group, an amino group or substituted amino group, a pyrrolidino, piperidino, hydrazino, morpholino, piperazino or substituted piperazino group, where the alkyl radicals may in each case be straight-chain or branched, and
A denotes a pyridine ring, where ring A may also be present in partially hydrogenated form,
and the tautomeric forms, salts and acid-addition salts thereof, processes for the preparation thereof, and the use thereof, and preparations which contain these compounds.

For reasons of simplicity, the compounds according to the invention are defined only in a tautomeric form which is represented by the formula I. However, the invention extends to all tautomeric forms of the compounds.

Although pharmaceutically acceptable salts and acid-addition salts of the compounds of the formula I are preferred, all salts come within the scope of the invention. All salts are valuable for the preparation of bases, even when the specific salt is only desired as an intermediate, such as, for example, when the salt is only formed for the purposes of purification or identification, or when it is used as an intermediate in the preparation of a pharmaceutically acceptable salt, such as, for example, by ion-exchange procedures.

The compounds of the general formula I, and the salts thereof, contain asymmetrical carbon atoms. The various optical isomers and the diastereoisomers are therefore also subject-matter of the invention, as are the salts and addition salts of these compounds with acids. Racemates can be resolved into their optical antipodes by methods which are known per se.

Preferred compounds of the formula I are those having an aromatic A ring in which at least one of the substituents R$^1$, R$^2$, R$^3$ or R$^4$ denotes a radical which is not hydrogen, and, if R$^4$ is bromine, at least one of the substituents R$^1$, R$^2$ or R$^3$ also denotes a radical which is not hydrogen.

Particularly preferred compounds are those of the formulae Ia and Ib

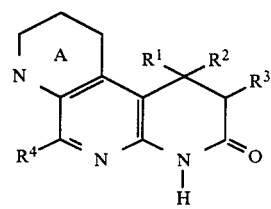

(Ia)

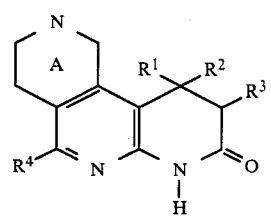

(Ib)

in which R$^1$, R$^2$, R$^3$, R$^4$ and A have the abovementioned meaning. In particular, A is pyrido in this case and is therefore aromatic, corresponding to the formula Ia' and Ib'.

The alkyl groups according to the invention and the alkyl parts of other groups, such as the alkylthio, ester and alkoxy groups, may be straight-chain or branched, and are preferably methyl, ethyl, propyl and butyl groups. Aryl is preferably carbocyclic aryl.

Halogen is fluorine, chlorine, bromine or iodine, preferably bromine.

The substituents R$^1$ and/or R$^2$ are preferably alkyl, in particular methyl, ethyl, propyl and isopropyl.

Preferred cycloalkyl groups are carbocyclic cycloalkyl groups, such as the cyclopropyl, cyclobutyl, cyclopentyl and cyclohexyl group.

Alkoxy carbonyl groups R$^1$ and R$^3$ are preferably lower ester groups, in particular methoxycarbonyl, ethoxycarbonyl and propoxycarbonyl groups.

The substituents R$^2$ and R$^3$ are preferably hydrogen. R$^2$ is preferably hydrogen when R$^1$ denotes a radical other than hydrogen or denotes methyl.

Preferred radicals R$^4$ are halogen, preferably chlorine or bromine, cyano, hydroxyl, alkoxy, in particular methoxy and ethoxy groups, and, in particular, the amino group and substituted amino groups.

Aryloxy groups are preferably carbocyclic aryloxy groups, in particular phenoxy groups.

Preferred substituted amino groups, which form the substituents of the alkylthio or alkoxy groups, are mono- or dialkylated amino groups having up to 6, preferably up to 3, carbon atoms per alkyl radical.

Substituted amino groups R$^4$ are acylamino groups or monosubstituted or, preferably, disubstituted amino groups, in particular alkylamino groups. These alkyl groups may be straight-chain or branched and contain 1 to 6, preferably 1 to 3, carbon atoms, and they may likewise be substituted. Preferred substituents of the alkyl groups are carbocyclic aryl groups, in particular the phenyl group. Particularly preferred substituents of the amino group are carbocyclic arylalkyl groups, in particular aryl(lower alkyl) groups, preferably benzyl groups.

Preferred acyl radicals of the acylamino groups are formyl and alkylcarbonyl, in particular having 1 to 3 carbon atoms in the alkyl part, for example acetyl.

Further preferred substituted amino groups $R^4$ are preferably piperazine groups which are unsubstituted or substituted in the 4-position, and the hydrazino group. The substituted piperazine group preferably carries an alkoxycarbonyl group, in particular the methoxycarbonyl, ethoxycarbonyl or propoxycarbonyl group, or a benzyl group.

Particularly preferred substituted amino groups $R^4$ are monosubstituted or disubstituted amino groups $NR^5R^6$, in which $R^5$ and $R^6$ which may be identical or different, are hydrogen, carbocyclic arylalkyl groups or branched or unbranched alkyl groups, in each case having 1 to 6 carbon atoms, which may optionally be substituted by alkoxy, aryloxy or substituted aryloxy groups, pyridinyl groups, cycloalkyl groups or substituted amino groups.

The alkoxy substituents of the alkyl groups $R^5$ and $R^6$ are preferably straight-chain or branched and have, in particular, 1 to 6, preferably 1 to 3, carbon atoms. Aryloxy is preferably phenoxy, and preferred substituents for this are straight-chain or branched alkoxy groups, in particular having 1 to 6, preferably 1 to 3, carbon atoms. The 2-methoxyphenoxy group is particularly preferred.

Substituted amino groups which form the substituents of the alkyl groups $R^5$ and $R^6$ are preferably monoalkylated or dialkylated amino groups in each case having 1 to 6, in particular 1 to 3, carbon atoms, or cyclic amino groups, such as the pyrrolidino, piperidino, morpholino, piperazino or substituted piperazino group. Preferred substituents of these, in particular piperazino substituents, are aryl, if appropriate substituted aryl, in particular alkoxyphenyl groups. The piperazino group is preferably substituted in the 1,4-position. The 2-methoxyphenylpiperazino group is particularly preferred.

Together with the carbon atoms in the 7- and 8-position of the bond c of the naphthyridine structure, the ring A forms a pyridine ring whose nitrogen in each case occupies one of the four remaining positions 7, 8, 9 and 10 of the pyridonaphthyridine structure, and which may also, if appropriate, be partially hydrogenated. Preferred compounds are those of the formula I, in which the nitrogen atom is located in the 7-position. These are the pyrido[2,3-c][1,8]naphthyridinones of the formula Ia. Compounds of the formula I in which the nitrogen atom is located in the 9-position are likewise preferred. These are the pyrido[4,3-c][1,8]naphthyridinones of the formula Ib. Particularly preferred compounds are those of the formulae Ia or Ib having an aromatic pyrido radical A (formulae Ia' and Ib').

The 7-, 8-, 9- and 10- positions of the pyrido[1,8]naphthyridine structure may be completely, partially or not hydrogenated, so that double bonds may be present in the 7,8- and/or 9,10- or 8,9-position. Of these, the unhydrogenated, aromatic compounds and the 7,8,9,10-tetrahydro compounds, but in particular the aromatic compounds, are preferred.

Besides the compounds mentioned in the examples, the following compounds according to the invention, and the salts thereof, are preferred:

1-methyl-6-bromo-1,2-dihydropyrido[2,3-c][1,8]naphthyridin-3(4H)-one 1-methyl-1,2-dihydropyrido[2,3-c][1,8]naphthyridin-3(4H)-one 1-methyl-6-methoxy-1,2-dihydropyrido[2,3-c][1,8]naphthyridin-3(4H)-one 1-methyl-6-ethoxy-1,2-dihydropyrido[2,3-c][1,8]naphthyridin-3(4H)-one 1-methyl-6-propoxy-1,2-dihydropyrido[2,3-c][1,8]naphthyridin-3(4H)-one 1-methyl-6-methylamino-1,2-dihydropyrido[2,3-c][1,8]naphthyridin-3(4H)-one 1-methyl-6-dimethylamino-1,2-dihydropyrido[2,3-c][1,8]naphthyridin-3(4H)-one 1-methyl-6-ethylamino-1,2-dihydropyrido[2,3-c][1,8]naphthyridin-3(4H)-one 1-methyl-6-diethylamino-1,2-dihydropyrido[2,3-c][1,8]naphthyridin-3(4H)-one 1-methyl-6-n-propylamino-1,2-dihydropyrido[2,3-c][1,8]naphthyridin-3(4H)-one 1-methyl-6-isopropylamino-1,2-dihydropyrido[2,3-c][1,8]naphthyridin-3(4H)-one 1-methyl-6-n-butylamino-1,2-dihydropyrido[2,3-c][1,8]naphthyridin-3(4H)-one 1-methyl-6-cyano-1,2-dihydropyrido[2,3-c][1,8]naphthyridin-3(4H)-one 1-methyl-6-acetamido-1,2-dihydropyrido[2,3-c][1,8]naphthyridin-3(4H)-one 1-methyl-6-(4-benzyl-1-piperazino)-1,2-dihydropyrido[2,3-c][1,8]naphthyridin-3(4H)-one 1-methyl-6-[2-[4-(2-methoxyphenyl)-1-piperazinyl]ethylamino]-1,2-dihydropyrido[2,3-c][1,8]naphthyridin-3(4H)-one 1-methyl-6-carbamoyl-1,2-dihydropyrido[2,3-c][1,8]naphthyridin-3(4H)-one 6-bromo-1,2-dihydropyrido[2,3-c][1,8]naphthyridin-3(4H)-one 6-methylamino-1,2-dihydropyrido[2,3-c][1,8]naphthyridin-3(4H)-one 6-dimethylamino-1,2-dihydropyrido[2,3-c][1,8]naphthyridin-3(4H)-one 6-ethylamino-1,2-dihydropyrido[2,3-c][1,8]naphthyridin-3(4H)-one 6-diethylamino-1,2-dihydropyrido[2,3-c][1,8]naphthyridin-3(4H)-one 6-n-propylamino-1,2-dihydropyrido[2,3-c][1,8]naphthyridin-3(4H)-one 6-isopropylamino-1,2-dihydropyrido[2,3-c][1,8]naphthyridin-3(4H)-one 6-n-butylamino-1,2-dihydropyrido[2,3-c][1,8]naphthyridin-3(4H)-one 6-cyano-1,2-dihydropyrido[2,3-c][1,8]naphthyridin-3(4H)-one 6-[2-[4-(2-methoxyphenyl)-1-piperazinyl]-ethylamino]-1,2-dihydropyrido[2,3-c][1,8]naphthyridin-3(4H)-one 1-isopropyl-6-bromo-1,2-dihydropyrido[2,3-c][1,8]naphthyridin-3(4H)-one 1-isopropyl-6-methylamino-1,2-dihydropyrido[2,3-c][1,8]naphthyridin-3(4H)-one 1-isopropyl-6-dimethylamino-1,2-dihydropyrido[2,3-c]1,8]naphthyridin-3(4H)-one 1-isopropyl-6-ethylamino-1,2-dihydropyrido[2,3-c][1,8]naphthyridin-3(4H)-one 1-isopropyl-6-diethylamino-1,2-dihydropyrido[2,3-c]1,8]naphthyridin-3(4H)-one 1-isopropyl-6-n-propylamino-1,2-dihydropyrido[2,3-c]1,8]naphthyridin-3(4H)-one 1-isopropyl-6-isopropylamino-1,2-dihydropyrido[2,3-c]1,8]naphthyridin-3(4H)-one 1-isopropyl-6-n-butylamino-1,2-dihydropyrido[2,3-c][1,8]naphthyridin-3(4H)-one
1-isopropyl-6-cyano-1,2-dihydropyrido[2,3-c][1,8]naphthyridin-3(4H)-one
1-isopropyl-6-[2-[4-(2-methoxyphenyl)-1-piperazinyl]ethylamino]-1,2-dihydropyrido[2,3-c][1,8]naphthyridin-3(4H)-one
1-methyl-6-bromo-1,2-dihydropyrido[3,4-c][1,8]naphthyridin-3(4H)-one
1-methyl-1,2-dihydropyrido[3,4-c][1,8]naphthyridin3(4H)-one
1-methy-6-methoxy-1,2-dihydropyrido[3,4-c][1,8]naphtyridin-3(4H)-one
1-methyl-6-ethoxy-1,2-dihydropyrido[3,4-c][1,8]naphthyridin-3(4H)-one
1-methyl-6-propoxy-1,2-dihydropyrido[3,4-c][1,8]naphthyridin-3(4H)-one
1-methyl-6-methylamino-1,2-dihydropyrido[3,4-c][1,8]naphthyridin-3(4H)-one
1-methyl-6-dimethylamino-1,2-dihydropyrido[3,4-c][1,8]naphthyridin-3(4H)-one
1-methyl-6-ethylamino-1,2-dihydropyrido[3,4-c][1,8]naphthyridin-3(4H)-one
1-methyl-6-diethylamino-1,2-dihydropyrido[3,4-c][1,8]naphthyridin-3(4H)-one
1-methyl-6-n-propylamino-1,2-dihydropyrido[3,4-c][1,8]naphthyridin-3(4H)-one
1-methyl-6-isopropylamino-1,2-dihydropyrido[3,4-c][1,8]naphthyridin-3(4H)-one
1-methyl-6-n-butylamino-1,2-dihydropyrido[3,4-c][1,8]naphthyridin-3(4H)-one
1-methyl-6-cyano-1,2-dihydropyrido[3,4-c][1,8]naphthyridin-3(4H)-one
1-methyl-6-acetamido-1,2-dihydropyrido[3,4-c][1,8]naphthyridin-3(4H)-one
1-methyl-6-(4-benzyl-1-piperazino)-1,2-dihydropyrido[3,4-c][1,8]naphthyridin-3(4H)-one
1-methyl-6-[2-[4-(2-methoxy-phenyl)-1-piperazinyl]ethylamino]-1,2-dihydropyrido[3,4-c][1,8]naphthyridin-3(4H)-one
1-methyl-6-carbamoyl-1,2-dihydropyrido[3,4-c][1,8]naphthyridin-3(4H)-one
6-bromo-1,2-dihydropyrido[3,4-c][1,8]naphthyridin-3(4H)-one
6-methylamino-1,2-dihydropyrido[3,4-c][1,8]naphthyridin-3(4H)-one
6-dimethylamino-1,2-dihydropyrido[3,4-c][1,8]naphthyridin-3(4H)-one
6-ethylamino-1,2-dihydropyrido[3,4-c][1,8]naphthyridin-3(4H)-one
6-diethylamino-1,2-dihydropyrido[3,4-c][1,8]naphthyridin-3(4H)-one
6-n-propylamino-1,2-dihydropyrido[3,4-c][1,8]naphthyridin-3(4H)-one
6-isopropylamino-1,2-dihydropyrido[3,4-c][1,8]naphthyridin-3(4H)-one
6-n-butylamino-1,2-dihydropyrido[3,4-c][1,8]naphthyridin-3(4H)-one
6-cyano-1,2-dihydropyrido[3,4-c][1,8]naphthyridin-3(4H)-one
6-[2-[4-(2-methoxyphenyl)-1-piperazinyl]-ethylamino]1,2-dihydropyrido[3,4-c][1,8]naphthyridin-3(4H)-one
1-isopropyl-6-bromo-1,2-dihydropyrido[3,4-c][1,8]naphthyridin-3(4H)-one
1-isopropyl-6-methylamino-1,2-dihydropyrido[3,4-c][1,8]naphthyridin-3(4H)-one
1-isopropyl-6-dimethylamino-1,2-dihydropyrido[3,4-c][1,8]naphthyridin-3(4H)-one
1-isopropyl-6-ethylamino-1,2-dihydropyrido[3,4-c][1,8]naphthyridin-3(4H)-one
1-isopropyl-6-diethylamino-1,2-dihydropyrido[3,4-c][1,8]naphthyridin-3(4H)-one
1-isopropyl-6-n-propylamino-1,2-dihydropyrido[3,4-c][1,8]naphthyridin-3(4H)-one
1-isopropyl-6-isopropylamino-1,2-dihydropyrido[3,4-c][1,8]naphthyridin-3(4H)-one
1-isopropyl-6-n-butylamino-1,2-dihydropyrido[3,4-c][1,8]naphthyridin-3(4H)-one
1-isopropyl-6-cyano-1,2-dihydropyrido[3,4-c][1,8]naphthyridin-3(4H)-one
1-isopropyl-6-[2-[4-(2-methoxyphenyl)-1-piperazinyl]ethylamino]-1,2-dihydropyrido[3,4-c][1,8]naphthyridin-3(4H)-one
6-isopropylamino-1,2-dihydropyrido[3,4-c][1,8]naphthyridin-3(4H)-one
6-n-butylamino-1,2-dihydropyrido[3,4-c][1,8]naphthyridin-3(4H)-one
6-cyano-1,2-dihydropyrido[3,4-c][1,8]naphthyridin-3(4H)-one
6-[2-[4-(2-methoxyphenyl)-1-piperazinyl]-ethylamino]-1,2-dihydropyrido[3,4-c[1,8]naphthyridin-3(4H)-one
1-isopropyl-6-bromo-1,2-dihydropyrido[3,4-c][1,8]naphthyridin-3(4H)-one
1-isopropyl-6-methylamino-1,2-dihydropyrido[3,4-c][1,8]naphthyridin-3(4H)-one
1-isopropyl-6-dimethylamino-1,2-dihydropyrido[3,4-c]1,8]naphthyridin-3(4H)-one
1-isopropyl-6-ethylamino-1,2-dihydropyrido[3,4-c][1,8]naphthyridin-3(4H)-one
1-isopropyl-6-diethylamino-1,2-dihydropyrido[3,4-c]1,8]naphthyridin-3(4H)-one
1-isopropyl-6-n-propylamino-1,2-dihydropyrido[3,4-c]1,8]naphthyridin-3(4H)-one
1-isopropyl-6-isopropylamino-1,2-dihydropyrido[3,4-c]1,8]naphthyridin-3(4H)-one
1-isopropyl-6-n-butylamino-1,2-dihydropyrido[3,4-c]1,8]naphthyridin-3(4H)-one
1-isopropyl-6-cyano-1,2-dihydropyrido[3,4-c][1,8]naphthyridin-3(4H)-one
1-isopropyl-6-[2-[4-(2-methoxyphenyl)-1-piperazinyl]ethylamino]-1,2-dihydropyrido[3,4-c][1,8]naphthyridin-3(4H)-one
1-methyl-6-bromo-1,2-dihydropyrido[4,3-c][1,8]naphthyridin-3(4H)-one
1-methyl-1,2-dihydropyrido[4,3-c][1,8]naphthyridin-3(4H)-one
1-methyl-6-methoxy-1,2-dihydropyrido[4,3-c][1,8]naphthyridin-3(4H)-one
1-methyl-6-ethoxy-1,2-dihydropyrido[4,3-c][1,8]naphthyridin-3(4H)-one
1-methyl-6-propoxy-1,2-dihydropyrido[4,3-c][1,8]naphthyridin-3(4H)-one
1-methyl-6-methylamino-1,2-dihydropyrido[4,3-c][1,8]naphthyridin-3(4H)-one
1-methyl-6-dimethylamino-1,2-dihydropyrido[4,3-c][1,8]naphthyridin-3(4H)-one
1-methyl-6-ethylamino-1,2-dihdropyrido[4,3-c][1,8]naphthyridin-3(4H)-one
1-methyl-6-diethylamino-1,2-dihydropyrido[4,3-c][1,8]naphthyridin-3(4H)-one
1-methyl-6-n-propylamino-1,2-dihydropyrido[4,3-c][1,8]naphthyridin-3(4H)-one
1-methyl-6-isopropylamino-1,2-dihydropyrido[4,3-c][1,8]naphthyridin-3(4H)-one 1-methyl-6-n-butylamino-1,2-dihydropyrido[4,3-c][1,8]naphthyridin-3(4H)-one
1-methyl-6-cyano-1,2-dihydropyrido[4,3-c][1,8]naphthyridin-3(4H)-one
1-methyl-6-acetamido-1,2-dihydropyrido[4,3-c][1,8]naphthyridin-3(4H)-one
1-methyl-6-(4-benzyl-1-piperazino)-1,2-dihydropyrido4,3-c][1,8]naphthyridin-3(4H)-one
1-methyl-6-[2-[4-(2-methoxyphenyl)-1-piperazinyl]ethylamino]-1,2-dihydropyrido[4,3-c][1,8]naphthyridin-3(4H)-one
1-methyl-6-carbamoyl-1,2-dihydropyrido[4,3-][1,8]naphthyridin-3(4H)-one
6-bromo-1,2-dihydropyrido[4,3-c][1,8]naphthyridin-3(4H)-one
6-methylamino-1,2-dihydropyrido[4,3-c][1,8]naphthyridin-3(4H)-one
6-dimethylamino-1,2-dihydropyrido[4,3-c][1,8]naphthyridin-3(4H)-one
6-ethylamino-1,2-dihydropyrido[4,3-c][1,8]naphthyridin-3(4H)-one
6-diethylamino-1,2-dihydropyrido[4,3-][1,8]naphthyridin-3(4H)-one
6-n-propylamino-1,2-dihydropyrido[4,3-c][1,8]naphthyridin-3(4H)-one
6-isopropylamino-1,2-dihydropyrido[4,3-c][1,8]naphthyridin-3(4H)-one
6-n-butylamino-1,2-dihydropyrido[4,3-c][1,8]naphthyridin-3(4H)-one
6-cyano-1,2-dihydropyrido[4,3-c][1,8]naphthyridin-3(4H)-one
6-[2-[4-(2-methoxyphenyl)-1-piperazinyl]ethylamino]1,2-dihydropyrido[4,3-c][1,8]naphthyridin-3(4H)-one
1-isopropyl-6-bromo-1,2-dihydropyrido[4,3-c][1,8]naphthyridin-3(4H)-one
1-isopropyl-6-methylamino-1,2-dihydropyrido[4,3-c][1,8]naphthyridin-3(4H)-one
1-isopropyl-6-dimethylamino-1,2-dihydropyrido[4,3-c][1,8]naphthyridin-3(4H)-one
1-isopropyl-6-ethylamino-1,2-dihydropyrido[4,3-c][1,8]naphthyridin-3(4H)-one
1-isopropyl-6-diethylamino-1,2-dihydropyrido[4,3-c][1,8]naphthyridin-3(4H)-one
1-isopropyl-6-n-propylamino-1,2-dihydropyrido[4,3-c]1,8]naphthyridin-3(4H)-one
1-isopropyl-6-isopropylamino-1,2-dihydropyrido[4,3-c][1,8]naphthyridin-3(4H)-one
1-isopropyl-6-n-butylamino-1,2-dihydropyrido[4,3-c][1,8]naphthyridin-3(4H)-one
1-isopropyl-6-cyano-1,2-dihydropyrido[4,3-c][1,8]naphthyridin-3(4H)-one
1-isopropyl-6[4-(2-methoxyphenyl)-1-piperazinyl]ethylamino]-1,2-dihydropyrido[4,3-c][1,8]naphthyridin-3(4H)-one
1methyl-6-bromo-1,2-dihydropyrido[3,2-c][1,8]naphthyridin-3(4H)-one
1-methyl-1,2-dihydropyrido[3,2-c][1,8]naphthyridin-3(4H)-one
1-methyl-6-methoxy-1,2-dihydropyrido[3,2-c][1,8]naphthyridin-3(4H)-one
1-methyl-6-ethoxy-1,2-dihydropyrido[3,2-c][1,8]naphthyridin-3(4H)-one
1-methyl-6-propoxy-1,2-dihydropyrido[3,2-c][1,8]naphthyridin-3(4H)-one
1-methyl-6-methylamino-1,2-dihydropyrido[3,2-c][1,8]naphthyridin-3(4H)-one
1-methyl-6-dimethylamino-1,2-dihydropyrido[3,2-c][1,8]naphthyridin-3(4H)-one
1-methyl-6-ethylamino-1,2-dihydropyrido[3,2-c][1,8]naphthyridin-3(4H)-one
1-methyl-6-diethylamino-1,2-dihydropyrido[3,2-c][1,8]naphthyridin-3(4H)-one
1-methyl-6-n-propylamino-1,2-dihydropyrido[3,2-c][1,-8--naphthyridin-3(4H)-one
1-methyl-6-isopropylamino-1,2-dihydropyrido[3,2-c][1,8]naphthyridin-3(4H)-one
1-methyl-6-n-butylamino-1,2-dihydropyrido[3,2-c][1,8]naphthyridin-3(4H)-one
1-methyl-6-cyano-1,2-dihydropyrido[3,2-c][1,8]naphthyridin-3(4H)-one
1-methyl-6-acetamido-1,2-dihydropyrido[3,2-c][1,8]naphthyridin-3(4H)-one
1-methyl-6-(4-benzyl-1-piperazino)-1,2-dihydropyrido3,2-c][1,8]naphthyridin-3(4H)-one
1-methyl-6-[2-[4-(2-methoxy-phenyl)-1-piperazinyl]ethylamino]-1,2-dihydropyrido[3,2-c][1,8]naphthyridin-3(4H)-one
1-methyl-6-carbamoyl-1,2-dihydropyrido[3,2-c][1,8]naphthyridin-3(4H)-one
6-bromo-1,2-dihydropyrido[3,2-c][1,8]naphthyridin-3(4H)-one
6-methylamino-1,2-dihydropyrido[3,2-c][1,8]naphthyridin-3(4H)-one
6-dimethylamino-1,2-dihydropyrido[3,2-c][1,8]naphthyridin-3(4H)-one
6-ethylamino-1,2-dihydropyrido[3,2-c][1,8]naphthyridin-3(4H)-one
6-diethylamino-1,2-dihydropyrido[3,2-c][1,8]naphthyridin-3(4H)-one
6-n-propylamino-1,2-dihydropyrido[3,2-c][1,8]naphthyridin-3(4H)-one
6-isopropylamino-1,2-dihydropyrido[3,2-c][1,8]naphthyridin-3(4H)-one
6-n-butylamino-1,2-dihydropyrido[3,2-c][1,8]naphthyridin-3(4H)-one
6-cyano-1,2-dihydropyrido[3,2-c][1,8]naphthyridin-3(4H)-one
6-[2-[4-(2-methoxyphenyl)-1-piperazinyl]-ethylamino]-1,2-dihydropyrido[3,2-c][1,8]naphthyridin-3(4H)-one
1-isopropyl-6-bromo-1,2-dihydropyrido[3,2-c][1,8]naphthyridin-3(4H)-one
1-isopropyl-6-methylamino-1,2-dihydropyrido[3,2-c][1,8]naphthyridin-3(4H)-one
1-isopropyl-6-dimethylamino-1,2-dihydropyrido[3,2-c]1,8]naphthyridin-3(4H)-one
1-isopropyl-6-ethylamino-1,2-dihydropyrido[3,2-c][1,8]naphthyridin-3(4H)-one
1-isopropyl-6-diethylamino-1,2-dihydropyrido[3,2-c][1,8]naphthyridin-3(4H)-one
1-isopropyl-6-n-propylamino-1,2-dihydropyrido[3,2-c][1,8]naphthyridin-3(4H)-one
1-isopropyl-6-isopropylamino-1,2-dihydropyrido[3,2-c][1,8]naphthyridin-3(4H)-one
1-isopropyl-6-n-butylamino-1,2-dihydropyrido[3,2-c][1,8]naphthyridin-3(4H)-one
1-isopropyl-6-cyano-1,2-dihydropyrido[3,2-c][1,8]naphthyridin-3(4H)-one
1-isopropyl-6-[2-[4-(2-methoxyphenyl)-1-piperazinyl]ethylamino]-1,2-dihydropyrido[3,2-c][1,8]naphthyridin-3(4H)-one
1-methyl-6-phenoxy-1,2-dihydropyrido[4,3-c][1,8]naphthyridin-3(4H)-one
1-n-hexyl-6-bromo-1,2-dihydropyrido[2,3-c][1,8]naphthyridin-3(4H)-one
1-cyclohexyl-6-isopropylamino-1,2-d:hydropyrido[4,3-c]1,8]naphthyridin-3(4H)-one 1,1-dimethyl-6-methylamino-1,2-dihydropyrido[4,3-c]1,8]naphthyridin-3(4H)-one
1-methyl-2-carbamoyl-6-bromo-1,2-dihydropyrido[4,3-c][1,8]naphthyridin-3(4H)-one
1-methyl-2-ethyl-6-methylamino-1,2-dihydropyrido[4,3-c][1,8]naphthyridin-3(4H)one
1-methyl-6-hydroxy-1,2-dihydropyrido[2,3-c][1,8]naphthyridin-3(4H)-one
1-phenyl-6-bromo-1,2-dihydropyrido[2,3-c][1,8]naphthyridin-3(4H)-one
1-ethoxycarbonyl-6-bromo-1,2-dihydropyrido[2,3-c][1,8]naphthyridin-3(4H)-one
1-carboxy-6-bromo-1,2-dihydropyrido[2,3-c][1,8]naphthyridin-3(4H)-one
1-carbamoyl-6-bromo-1,2-dihydropyrido[2,3-c][1,8]naphthyridin-3(4H)-one
1-cyano-6-bromo-1,2-dihydropyrido[2,3-c][1,8]naphthyridin-3(4H)-one
1-methyl-2-carboxy-6-bromo-1,2-dihydropyrido[4,3-c][1,8]naphthyridin-3(4H)-one
1-methyl-2-methoxycarbonyl-6-bromo-1,2-dihydropyrido[4,3-c][1,8]naphthyridin-3(4H)-one
1-methyl-2-cyano-6-bromo-1,2-dihydropyrido[4,3-c][1,8]naphthyridin-3(4H)-one
1-methyl-6-methylsulphido-1,2-dihydropyrido[2,3-c][1,8]naphthyridin-3(4H)-one
1-methyl-6-(2-dimethylaminoethoxy)-1,2-dihydropyrido[2,3-c][1,8]naphthyridin-3(4H)-one
1-methyl-6-(2-dimethylaminoethylsulphido)-1,2-dihydropyrido[2,3-c][1,8]naphthyridin-3(4H)-one
1-methyl-6-amino-1,2-dihydropyrido[2,3-c][1,8]naphthyridin-3(4H)-one
1-methyl-6-pyrrolidino-1,2-dihydropyrido[2,3-c][1,8]naphthyridin-3(4H)-one
1-methyl-6-piperidino-1,2-dihydropyrido[2,3-c][1,8]naphthyridin-3(4H)-one
1-methyl-6-hydrazino-1,2-dihydropyrido[2,3-c][1,8]naphthyridin-3(4H)-one
1-methyl-6-morpholino-1,2-dihydropyrido[2,3-c][1,8]naphthyridin-3(4H)-one
1-methyl-6-piperazino-1,2-dihydropyrido[2,3-c][1,8]naphthyridin-3(4H)-one The following compounds of the general formula I, and the salts thereof having a high therapeutic effect, are particularly preferred, to be precise in the form of the racemates and in the form of optically active isomers:

1-methyl-6-bromo-1,2-dihydropyrido[2,3-c][1,8]naphthyridin-3(4H)-one
1-methyl-6-methylamino-1,2-dihydropyrido[2,3-c][1,8]naphthyridin-3(4H)-one
1-methyl-6-ethylamino-1,2-dihydropyrido[2,3-c][1,8]naphthyridin-3(4H)-one
1-methyl-6-n-propylamino-1,2-dihydropyrido[2,3-c][1,8]naphthyridin-3(4H)-one
1-methyl-6-isopropylamino-1,2-dihydropyrido[2,3-c][1,8]naphthyridin-3(4H)-one
1-methyl-6-dimethylamino-1,2-dihydropyrido[2,3-c][1,8]naphthyridin-3(4H)-one
1-methyl-6-diethylamino-1,2-dihydropyrido[2,3-c][1,8]naphthyridin-3(4H)-one
1-methyl-6-di-n-propylamino-1,2-dihydropyrido[2,3-c][1,8]naphthyridin-3(4H)-one
1-methyl-6-diisopropylamino-1,2-dihydropyrido[2,3-c][1,8]naphthyridin-3(4H)-one
1-methyl-6-[2-[4-(2-methoxyphenyl)-1-piperazinyl]ethylamino]-1,2-dihydropyrido[2,3-c][1,8]naphthyridin-3(4H)-one
1-methyl-6-cyano-1,2-dihydropyrido[2,3-c][1,8]naphthyridin-3(4H)-one
1-methyl-6-bromo-1,2-dihydropyrido[4,3-c][1,8]naphthyridin-3(4H)-one
1-methyl-6-methylamino-1,2-dihydropyrido[4,3-c][1,8]naphthyridin-3(4H)-one
1-methyl-6-ethylamino-1,2-dihydropyrido[4,3-c][1,8]naphthyridin-3(4H)-one
1-methyl-6-n-propylamino-1,2-dihydropyrido[4,3-c][1,8]naphthyridin-3(4H)-one
1-methyl-6-isopropylamino-1,2-dihydropyrido[4,3-c][1,8]naphthyridin-3(4H)-one
1-methyl-6-dimethylamino-1,2-dihydropyrido[4,3-c][1,8]naphthyridin-3(4H)-one
1-methyl-6-diethylamino-1,2-dihydropyrido[4,3-c][1,8]naphthyridin-3(4H)-one
1-methyl-6-di-n-propylamino-1,2-dihydropyrido[4,3-c][1,8]naphthyridin-3(4H)-one
1-methyl-6-diisopropylamino-1,2-dihydropyrido[4,3-c][1,8]naphthyridin-3(4H)-one
1-methyl-6-cyano-1,2-dihydropyrido[4,3-c][1,8]naphthyridin-3(4H)-one
1-methyl-6-[2-[4-(2-methoxyphenyl)-1-piperazinyl]ethylamino]-1,2-dihydropyrido[4,3-c][1,8]naphthyridin-3(4H)-one The compounds of the formula I according to the invention, and the isomers thereof, and the physiologically acceptable salts and acid-addition salts thereof are therapeutic active ingredients, have a high pharmacological action and are valuable medicaments. In particular, they exhibit cardiovascular actions. They have a positive inotropic and vasodilatory properties and are therefore suitable for the treatment of heart insufficiency, in particular chronic heart insufficiency, angina pectoris and/or hypertonia.

Furthermore, the compounds can be used to reduce metastasis formation and for metastasis inhibition. In addition, they can be used for the treatment and prophylaxis of migraines, psoriasis and asthma, in particular bronchial asthma. The compounds inhibit thrombocyte aggregation. They can be used for the treatment and prophylaxis of thromboembolic disorders.

After i.v. administratiqn in dosages of 0.03 mg/kg–3 mg/kg in pigs and in i.v. administration of 0.1 mg/kg–1.0 mg/kg and i.d. administration of 0.1 mg/kg –10 mg/kg in cats, a relatively long-lasting blood pressure-reducing action, which is accompanied by a long-lasting positive inotropic effect, which can also be detected in vitro at the papillary muscle or atrium of the guinea-pig, is produced.

The compounds of the present invention can be administered orally or parenterally. The individual dosages for oral administration are 0.1–20 mg, preferably 0.5–10 mg, in particular 1–5 mg, in humans. These dosages are advantageous for the treatment of the above-mentioned disorders, in particular heart insufficiency.

Psoriasis can also be treated topically. Creams, lotions, ointments, solutions or powders which preferably contain the active ingredients in an amount of 1–10% are suitable, for example, for the treatment. For prophylaxis or treatments, a thin coating of the topical preparation is applied to the skin or affected skin once or several times daily.

According to the invention, pharmaceutical compositions which contain a compound of the formula I, or pharmaceutically acceptable salts thereof, together with a pharmaceutically acceptable diluent or excipient, are provided, and also topical preparations therewith, in particular creams, ointments, solutions, lotions and powders, which can be obtained in a fashion which is known per se.

The compounds according to the invention can be mixed with conventional pharmaceutically acceptable auxiliaries or excipients or also other substances and can be processed, for example, into oral, sublingual, parenteral, topical and rectal medicament forms and into drip solutions for application onto mucus membranes. They can be administered orally in the form of tablets, coated tablets, syrups, suspensions, hard and soft gelatin capsules and liquids or parenterally in the form of solutions or suspensions. Preparations to be administered orally can contain one or more additives, such as sweeteners, aromatization agents, colourants and preservatives. Tablets can contain the active ingredient along with conventional pharmaceutically acceptable auxiliaries, for example inert diluents, such as calcium carbonate, sodium carbonate, lactose and talc, granulation agents and agents which promote disintegration of the tablets in the case of oral administration, such as starch or alginic acid, binders, such as starch or gelatin, and lubricants, such as magnesium stearate, stearic acid and talc.

Suitable excipients are, for example, milk sugar (lactose), gelatin, maize starch, stearic acid, ethanol, propylene glycol, the ether of tetrahydrofurfuryl alcohol and water.

The tablets can be coated by known procedures in order to delay disintegration and resorption in the gastro-intestinal tract and also to prevent the incursion of gastric juice, by means of which the activity of the active ingredient can extend over a longer time span. The active ingredient in the suspensions can likewise be mixed with auxiliaries which are conventional for the preparation of such compositions, for example suspending agents, such as methylcellulose, tragacanth or sodium alginate, wetting agents, such as lecithin, polyoxyethylene stearate and polyoxyethylene sorbitan monooleate, and preservatives, such as ethyl para-hydroxybenzoate. Capsules can contain the active ingredient as the only component or mixed with a solid diluent, such as calcium carbonate, calcium phosphate or kaolin. Injectable preparations are likewise formulated in a fashion which is known per se. Pharmaceutical preparations can contain the active ingredient in an amount from 0.1 to 90%, in particular 1 to 90%, the remainder being an excipient or additive. With respect to the preparation and administration, solid preparations, such as tablets and capsules, are preferred. The preparations preferably contain the active ingredient in an amount of 5 to 10 mg.

The compounds of the formula I are prepared in that a compound of the general formula II

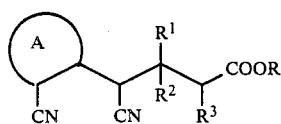

(II)

in which $R^1$, $R^2$ and $R^3$ have the abovementoned meaning, A is the pyridine ring and R denotes a lower alkyl group—preferably methyl or ethyl, is cyclized in a fashion which is known per se using a hydrohalic acid, in particular hydrobromic acid, to form compounds of the formula I where $R^4$ denotes a halogen atom (F. Johnson and W. A. Nasutaviens, J. Org. Chem. 27,3953 (1962)). The cyclization is preferably carried out using HBr/glacial acetic acid mixtures.

The preferred compounds of the formulae Ia and Ib are obtained, in particular, using the compounds of the formulae III and IV, in which R, $R^1$, $R^2$ and $R^3$ have the abovementioned meaning:

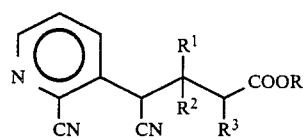

(III)

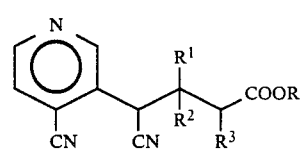

(IV)

The compounds of the general formula I in which $R^4$ has the other meanings specified are accessible from the compounds of the formula I where $R^4$=halogen, in particular bromine.

The compounds of the formula I in which $R^4$ denotes hydrogen are obtained through hydrogenation using hydrogen in the presence of a catalyst, in particular a palladium/activated charcoal catalyst, if appropriate with addition of sodium acetate. Other halogen radicals or the cyano group can be introduced in a fashion which is known per se using halides or cyanides, in particular using alkali metal halides or alkali metal cyanides, in particular potassium cyanide. The hydroxyl group can be introduced using bases, in particular alkali metal hydroxides. The abovementioned substitution reactions are preferably carried out at elevated temperature in a solvent. The carboxamide group is obtained from the cyano group by partial saponification.

In order to introduce the optionally also substituted alkoxy groups and aryloxy groups, the $R^4$ halogen compounds are heated with sodium alcoholate or potassium alcoholate in the corresponding alcohol. The optionally also substituted alkylthio compounds are obtained analogously from the corresponding mercaptans ($R^4$-H).

Compounds of the formula I carrying amino groups which are substituted in the 6-position or which are substituted in the 6-position by amino are obtained by substitution of $R^4$=halogen by an amine (of the formula H-$R^4$) corresponding to the above definition of the amino radicals, or ammonia in alcoholic solution at temperatures above 100° C., if appropriate under pressure. Included here are cyclic amines ($R^4$=pyrrolidino, piperidino, morpholino, piperazino and substituted piperazino) and hydrazine. For the preparation of amines which are acylated by $R^4$, compounds of the formula I in which $R^4$ denotes amino are reacted with an acylating agent, for example the appropriate carboxylic anhydride, the acylating agent serving as solvent.

The compounds of the formula I in which $R^1$ or $R^3$ symbolizes a carboxyl, carboxamide or cyano group are preferably prepared from the corresponding alkoxycarbonyl compounds by methods which are known from the literature. Other esters can be obtained in a fashion which is known per se by transesterification, and the free carboxylic acids can be obtained by cleaving the esters. Acid amides are obtained from esters by reacting with ammonia, and the compounds containing cyano groups are obtained by dehydrating the amides.

The compounds of the general formula I which are partially hydrogenated in the ring A (positions 7, 8, 9 and 10) are synthesized from the corresponding aromatic compounds of the formula I by reduction using hydrogen in the presence of a rhodium catalyst at 50-100 bar or are obtained in other, known, specific hydrogenation reactions.

The starting compounds of the general formula II can be prepared by Michael addition of
2-cyano-3-pyridyl-acetonitrile or
4-cyano-3-pyridyl-acetonitrile or
3-cyano-4-pyridyl-acetonitrile or
3-cyano-2-pyridyl-acetonitrile to propenoic acid esters of the general formula V

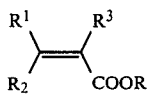

in which $R^1$, $R^2$, $R^3$ and R have the specified meanng. From 2-cyano-3-pyridyl-acetonitrile, the compounds of the formula Ia according to the invention are obtained after cyclization via the corresponding compounds of the formula II (or III), and from 4-cyano-3-pyridyl-acetonitrile, the compounds Ib are correspondingly obtained via II (or IV). The other pyrido[3,4-c][1,8]naphthyridinones having the nitrogen atom in the 8-position and the pyrido[3,2-c][1,8]naphthyridinones having the nitrogen atom in the 10-position can be synthesized in the same fashion.

The propenoic acid esters of the formula V are known or can be obtained by known methods.

The starting compounds of the formula II can likewise be formed by reacting the corresponding cyanoacetonitrile-lithium salts of the four cyanopyridylacetonitriles mentioned above with 3-bromopropionates of the general formula

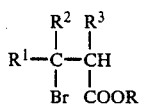

in an aprotic solvent, such as, for example, tetrahydrofuran, at temperatures below 0° C., $R^1$, $R^2$, $R^3$ and R having the specified meaning.

The starting compounds of the formula VI are known or can be obtained by known processes.

The compounds of the general formula I can be bases, acids or amphoteric and can thus be isolated from the reaction mixtures in the form of their salts or acid-addition salts. As bases, they can be converted into salts by known processes using suitable inorganic or organic acids, or, as acids, form salts with bases.

Physiologically acceptable salts or acid-addition salts are preferred. Inorganic salts which are suitable for this are, for example, hydrohalic acids, for example hydrochloric acid, or sulphuric acid, and organic acids which are suitable are, for example, fumaric acid, maleic acid, citric acid and tartaric acid. Preparation is carried out by adding the alcoholic solution of a suitable acid to the hot, alcoholic solution of the base, and the salt is obtained after adding ether. Preferred salts are the alkali metal salts, alkaline-earth metal salts and ammonium salts of the compounds of the formula I, these salts being obtained using the corresponding bases, in particular sodium hydroxide, potassium hydroxide or ammonium hydroxide.

Diastereoisomers can be resolved in a known fashion into their racemic modifications due to the physico-chemical differences of their components. Racemates can be resolved by known methods, for example by recrystallization in optically active solvents, by microorganisms or by reaction with an optically active acid or base which forms a salt with the racemic compound, resolution of the diastereoisomers by fractional crystallization and liberation of the enantiomers by suitable agents. Particularly suitable optically active acids are, for example, the D- and L-forms of tartaric acid, ditoluoyltartaric acid, malic acid, mandelic acid, camphorsulphonic acid or pyrrolidonecarboxylic acid. Suitable optically active bases are alpha-phenylethylamine, menthylamine, ephedrin, brucine and quinine. The more active of the antipodes is advantageously isolated. However, it is also possible according to the invention to obtain the pure enantiomers by asymmetrical synthesis.

The following examples illustrate the invention.

Example 1

Methyl 3-methyl-4-cyano-4-(2-cyano-3-pyridyl)butyrate

A catalytic amount of a 5% strength methanolic sodium methylate solution is added to a mixture of 4.9 g (0.03 mol) of 2-cyano-3-pyridylacetonitrile and 3.4 g (0.03 mol) of methyl crotonate with stirring at a rate such that the reaction temperature remains below 40° C. When the evolution of heat has subsided, the mixture is neutralized using dilute acetic acid. The mixture is extracted with chloroform and the organic phase is dried over $MgSO_4$, filtered and concentrated in vacuo. The residue is purified over a silica gel column using chloroform as eluent.

Yield: 6.0 g (82% of theory).

The following addition products of the formula II were obtained analogously from 2-cyano-3-pyridylacetonitrile and 4-cyano-3-pyridyl-acetonitrile and the corresponding propenoic acid esters:

Methyl 3-isopropyl-4-cyano-4-(2-cyano-3-pyridyl)butyrate

Methyl 3-methyl-4-cyano-4-(4-cyano-3-pyridyl)butyrate

Methyl 3-isopropyl-4-cyano-4-(4-cyano-3-pyridyl)butyrate

EXAMPLE 2

Methyl 4-cyano-4-(4-cyano-3-pyridyl)butyrate

An Li-diisopropylamide solution, prepared at minus 60° C. from 3.6 g (0.036 mol) of diisopropylamine in 30 ml of THF and 22.5 ml (0.036 mol) of a 1.6N butyllithium solution in hexane, is added dropwise at minus 60° C. to a solution of 5.1 g (0.036 mol) of 4-cyano-3-pyridylacetonitrile in 45 ml of THF.

When the addition is complete, this reaction mixture is introduced at minus 60° C. into a solution of 32.6 g (0.20 mol) of methyl 3-bromopropionate in 45 ml of THF.

The mixture is allowed to come to room temperature slowly, water is added, and the mixture is extracted with ethyl acetate. After drying and concentrating, the organic phase is purified via a silica gel column using chloroform as eluent.

Yield: 6.6 g (80% of theory)

Methyl 4-cyano-4-(2-cyano-3-pyridyl)butyrate was formed analogously.

EXAMPLE 3

1-Methyl-6-bromo-1,2-dihydropyrido[2,3-c][1,8]naphthyridin- 3(4H)-one 30.8 g (0.127 mol) of methyl 3-methyl-4-cyano 4-(2-cyano-3-pyridyl)butyrate are added dropwise with stirring and slight cooling in ice to 145 ml of 33% strength HBr/glacial acetic acid solution. The mixture is stirred for a further 2 hours at room temperature and subsequently allowed to stand overnight. A yellow precipitate deposits. The reaction mixture is added to NaHCO$_3$ solution, and the yellow precipitate is filtered off under suction, dried, and subsequently recrystallized from ethanol. 29.7 g (80% of theory) of 1-methyl-6-bromo-1,2-dihydropyrido[2,3-c][1,8]naphthyridin-3(4H)-one are obtained.

Melting point: 251°–252° C.

The following 1,2-dihydropyrido[1,8]naphthyridinones according to the invention of the formula VII, in which either X or Y denotes the pyrido nitrogen atom, corresponding to the formula Ia' (X=N, Y=CH) or Ib' (Y=N, X=CH), were formed analogously to Example 3:

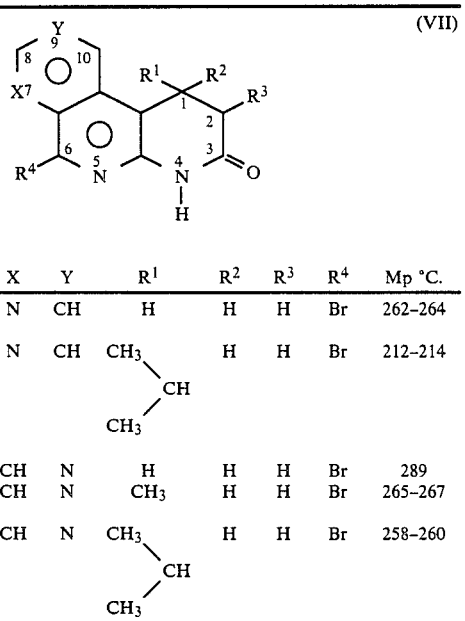

| Example No. | X | Y | R$^1$ | R$^2$ | R$^3$ | R$^4$ | Mp °C. |
|---|---|---|---|---|---|---|---|
| 4 | N | CH | H | H | H | Br | 262–264 |
| 5 | N | CH | CH$_3$\\CH/CH$_3$ | H | H | Br | 212–214 |
| 6 | CH | N | H | H | H | Br | 289 |
| 7 | CH | N | CH$_3$ | H | H | Br | 265–267 |
| 8 | CH | N | CH$_3$\\CH/CH$_3$ | H | H | Br | 258–260 |

EXAMPLE 9

-Methyl-6-isopropylamino-1,2-dihydropyrido[4,3-c][1,8]naphthyridin-3(4H)-one 3.6 g (0.012 mol) of 1-methyl-6-bromo-1,2-dihydropyrido[4,3-c][1,8]naphthyridin-3(4H)-one, 30 ml of absolute ethanol and 10 ml of isopropylamine are stirred for 6 hours at 160° C. in an autoclave. After cooling, the crystalline precipitate is filtered off under suction and recrystallized from methanol. 2.82 g (87% of theory) of 1-methyl-6-isopropylamino-1,2-dihydropyrido-[4,3-c][1,8]naphthyridin-3(4H)-one are obtained.

Melting point: 241°–242° C.

EXAMPLE 10

1-Methyl-6-[2-]4-(2-methoxyphenyl)-1-piperazinyl[ethylamino]-1,2-dihydropyrido[2,3-c][1,8]naphthyridin-3(4H)-one A solution of 1.5 g (0.005 mol) of 1-methyl-6-bromo-1,2-dihydropyrido[2,3-c][1,8]naphthyridin-3(4H)-one, 2.4 g (0.01 mol) of 2-[4-(2-methoxyphenyl)-1-piperazinyl]ethylamine, 0.5 g (0.005 mol) of triethylamine and 30 ml of n-butanol is refluxed for 6 hours at 140° C. The reaction mixture is concentrated, and the residue is distributed between water and chloroform. The organic phase is separated off, dried and concentrated. The residue is recrystallized from petroleum ether-/ethyl acetate.

0.8 g (35.8% of theory) of 1-methyl-6-[2-[4-(2-methoxyphenyl)-1-piperazinyl[ethylamino]-1,2-dihydropyrido [2,3-c][1,8]naphthyridin-3(4H)-one are obtained.

The following 1,2-dihydropyrido[1,8]naphthyridin-3(4H)-ones of the formula VII according to the invention were formed analogously to Examples 9 and 10.

| Example No. | x | y | R$^1$ | R$^2$ | R$^3$ | R$^4$ | m.p., °C. |
|---|---|---|---|---|---|---|---|
| 11 | N | CH | CH$_3$ | H | H | CH$_3$—NH— | 250–251 |
| 12 | N | CH | CH$_3$ | H | H | C$_6$H$_5$—CH$_2$—N⟨ ⟩N— | 192–193 |
| 13 | N | CH | H | H | H | CH$_3$—NH | 287–289 |
| 14 | N | CH | H | H | H | CH$_3$\\CH—NH/CH$_3$ | 195–197 |

-continued

| Example No. | x | y | R¹ | R² | R³ | R⁴ | m.p., °C. |
|---|---|---|---|---|---|---|---|
| 15 | N | CH | (CH₃)₂CH | H | H | CH₃NH | 235–236 |
| 16 | N | CH | (CH₃)₂CH | H | H | (CH₃)₂CH—NH | 235–236 |
| 17 | CH | N | CH₃ | H | H | CH₃—NH | >300 |
| 18 | CH | N | CH₃ | H | H | (CH₃)₂CH—NH | >300 |
| 19 | CH | N | CH₃ | H | H | 2-methoxyphenyl-piperazinyl-CH₂-CH₂-NH— | 199–200 |
| 20 | CH | N | H | H | H | CH₃—NH— | >320 |
| 21 | CH | N | H | H | H | (CH₃)₂CH—NH | 304–306 |
| 22 | CH | N | (CH₃)₂CH— | H | H | CH₃—NH— | 258–260 |
| 23 | CH | N | (CH₃)₂CH | H | H | (CH₃)₂CH—NH | 294–295 |

EXAMPLE 24

1-Methyl-6-cyano-1,2-dihydropyrido[2,3-c][1,8]naphthyridin-3(4H)-one 2 g (0.007 mol) of 1-methyl-6-bromo-1,2-dihydropyrido[2,3-c][1,8]naphthyridin-3(4H)-one, 0.3 g (0.003 mol) of CuCN and 0.3 g (0.005 mol) of KCN are heated for 7 hours at 160° C. in an autoclave with 20 ml of methanol and 10 ml of water. After cooling, the mixture is filtered under suction, and the residue digested in chloroform/methanol, 1:1, under reflux for 4 hours. The organic phase is filtered, dried and concentrated. The residue is purified by recrystallization from ethanol/petroleum ether, and 0.5 g (60.1% of theory) of 1-methyl-6-cyano-1,2-dihydropyrido[2,3-c][1,8]naphthyridin-3(4H)-one is obtained.

Melting point: above 300° C.

EXAMPLE 25

1-Isopropyl-6-cyano-1,2-dihydropyrido[2,3-c][1,8]naphthyridin-3(4H)-one 1.6 g (0.005 mol) of 1-isopropyl-6-bromo-1,2-dihydropyrido[2,3-c][1,8]naphthyridin-3(4H)-one are melted at 220° C. in a heavy-oil bath with 0.45 g (0.05 mol) of CuCN. After 1 hour, the melt is cooled, and the residue is ground in a mortar and stirred with concentrated ammonia solution. The precipitate is filtered off under suction, washed with water, dried and purified on a silica gel column with chloroform. 0.28 g (21% of theory) of 1-isopropyl-6-cyano-1,2-dihydropyrido[2,3-c][1,8]naphthyridin-3(4H)-one is obtained.

Melting point: 287°–299° C.

EXAMPLE 26

1-Methyl-6-carbamoyl-1,2-dihydropyrido[2,3-c][1,8]naphthyridin-3(4H)-one 2 g (0.008 mol) of 1-methyl-6-cyano-1,2-dihydropyrido[2,3-c][1,8]naphthyridin-3(4H)-one are allowed to stand for 3 hours at room temperature in 40 ml of 96% strength sulphuric acid. After neutralization using aqueous $Na_2CO_3$ solution, the mixture is extracted repeatedly with methylene chloride, the combined organic bases are dried and then evaporated in vacuo, and the residue is chromatographed on silica gel with chloroform/methanol 98:2. 1.29 g (63% of theory) of 1-methyl-6-carbamoyl-dihydropyrido[2,3-c][1,8]naphthyridin-3(4H)-one are obtained.

Melting point: 229° C. (decomposition).

EXAMPLE 27

1-Methyl-6-ethoxy-1,2-dihydropyrido[4,3-c][1,8]naphthyridin-3(4H)-one 1.5 g (0.005 mol) of 1-methyl-6-bromo-1,2-dihydropyrido[4,3-c][1,8]naphthyridin-3(4H)-one are dissolved in 20 ml of ethanol with 0.23 g (0.01 mol) of sodium, and the mixture is heated at 160° C. for 3 hours in an autoclave. The precipitated product is filtered off under suction, washed with ethanol and dried. 0.8 g (62.2% of theory) of 1-methyl-6-ethoxy-1,2-dihydropyrido[2,3-c][1,8]naphthyridin-3(4H)-one is obtained.

EXAMPLE 28

1-Methyl-1,2,7,8,9,10-hexahydropyrido[2,3-c][1,8]naphthyridin-3(4H)-one 1.5 g (0.005 mol) of 1-methyl-6-bromo-1,2-dihydropyrido[2,3-c][1,8]naphthyridin-3(4H)-one are hydrogenated for 24 hours at room temperature and atmospheric pressure in a mixture of 100 ml of ethanol and 100 ml of glacial acetic acid with Pd/C (0.3 g/10%) with addition of 0.4 g (0.005 mol) of Na-acetate. The catalyst is removed by filtration under suction, the filtrate is concentrated, and the residue is recrystallized from ethanol. 0.7 g (64.4% of theory) of 1-methyl-1,2,7,8,9,10-hexahydropyrido[2,3-c][1,8]naphthyridin-3(4H)one is obtained.

Melting point: 309°–311° C.

EXAMPLE 29

Preparation of tablets

Tablets which contain the components mentioned below can be prepared in a known fashion. They can be administered once or twice daily in a dosage of one tablet for treatment of the disorders mentioned above, in particular heart insufficiency:

| | |
|---|---|
| 1-methyl-6-isopropylamino-1,2-dihydropyrido-[4,3-c][1,8]naphthyridin-3(4H)-one | 4 mg |
| Lactose | 75 mg |
| Maize starch | 10 mg |
| Microcrystalline cellulose | 8 mg |
| Polyvinylpyrrolidone | 1 mg |
| Magnesium stearate | 0.5 mg |
| Highly disperse silicon dioxide | 0.5 mg |

EXAMPLE 30

A fatty ointment is prepared using the specified components (amounts by weight):

| | |
|---|---|
| White vaseline | 76% |
| Viscose paraffin | 15% |
| Glycerol | 2% |
| Emulsifier (polyoxyethylene-(40) stearate) | 2% |
| 1-methyl-6-isopropylamino-1,2-dihydropyrido-[2,3-c][1,8]naphthyridin-3(4H)-one | 5% |

The vaseline, paraffin, glycerol and emulsifier are heated to 80° C. the active ingredient is then added. The mixture is stirred until dissolution is effected, and the stirring is continued until solidification of the composition (ointment-like consistency).

The onintment is administered three times daily.

We claim:

1. Pyrido(1,8)naphthyridinones of the formula I

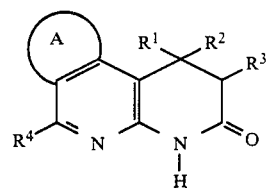

(I)

in which
R$^1$ denotes hydrogen, a straight-chain or branched alkyl group having 1 to 6 carbon atoms, a phenyl group or, a cycloalkyl group having 3 to 6 carbon atoms, a carboxyl group or a cyano group,
R$^2$ denotes hydrogen or a straight-chain or branched alkyl group having 1 to 4 carbon atoms,
R$^3$ denotes hydrogen, a straight-chain or branched alkyl group having 1 to 4 carbon atoms, a carboxyl group, a C$_1$–C$_3$-alkoxycarbonyl group, a carboxamide group or a cyano group,
R$^4$ denotes hydrogen, halogen, a cyano group, a hydroxyl group, a carboxamide group, an alkylthio group or an alkoxy group, in each case having 1 to 6 carbon atoms, which may in each case optionally be substituted by a mono or di-C$_1$–C$_6$-alkylated amino group, furthermore denotes a phenoxy group, an amino group, a formylamino group, a C$_1$–C$_3$-alkylcarbonylamino group, a pyrrolidino, a piperidino, hydrazino, morpholino, piperazino, a C$_1$–C$_3$-alkoxycarbonylpiperazino or benzylpiperazino group, or a monosubstituted or disubstituted amino group NR$^5$R$^6$,
R$^5$ and R$^6$ each independently is hydrogen, or branched or unbranched alkyl having 1 to 6 carbon atoms and optionally substituted by straight-chain or branched C$_1$–C$_6$-alkoxy, phenoxy or phenoxy substituted with straight-chain or branched C$_1$–C$_6$-alkoxy groups, pyridinyl groups, C$_3$–C$_6$-cycloalkyl groups, monoalkylated or dialkylated amino groups in each case having 1 to 6 carbon atoms, pyrrolidino, piperidino, morpholino, piperazino, 2-methoxyphenylpiperazino groups or phenyl groups, and
A denotes a pyridine ring, where ring A may also be present in partially hydrogenated form, and the tautomeric forms thereof, and the salts and acid addition salts thereof.

2. Compounds according to claim 1 of the formulae Ia′ and Ib′

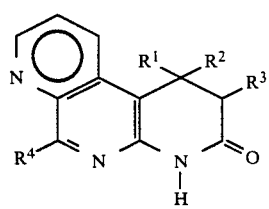

(Ia′)

-continued

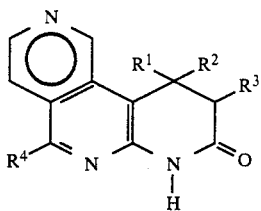
(Ib')

in which $R^1$, $R^2$, $R^3$ and $R^4$ have the abovementioned meaning, and the acid-addition salts thereof.

3. A compound of claim 1 which is 1-Methyl-6-isopropyl 1,2-dihydropyrido[4,3-c][1,8naphthyridin-3(4H)-one.

4. A compound of claim 1 which is 1-Methyl-6-bromo-1,2dihydropyrido4,3-c][1,8]naphthyridin-3(4H)-one.

5. A compound of claim 1 which is 1-Methyl-6-methylamino-2-dihydropyrido[4,3-c][1,8]naphthyridin-3(4H)-one.

6. A compound of claim 1 which is 1-Methyl-6-methylamino-1,2-dihydropyrido[2,3-c][1,8]naphthyridin-3(4H)-one.

7. A composition for the treatment of angina pectoris, for the reduction of metastatis formation, for metastasis inhibition, for the treatment and propylaxis of heart insufficiency, migraines, psoriasis and asthma and for the inhibition of thrombocyte aggregation comprising an amount effective therefor of a compound or salt according to claim 1 and a pharmaceutically acceptable diluent.

8. A method of treating angina pectoris, reducing formation of metastasis, for inhibiting metastasis, for treating heart insufficiency, migraines, psoriasis and asthma and for inhibitng thrombocyte aggregation which comprises administering to a patient in need thereof an amount effctive therefor of a compound or salt according to claim 1.

* * * * *

UNITED STATES PATENT AND TRADEMARK OFFICE
CERTIFICATE OF CORRECTION

PATENT NO. : 4,801,590

DATED : January 31, 1989

INVENTOR(S) : Erich Cohnen, et al

Page 1 of 2

It is certified that error appears in the above-identified patent and that said Letters Patent is hereby corrected as shown below:

| | |
|---|---|
| Title Page, Abstract, line 22 | Delete "piperazine" and substitute --piperazino-- |
| Col. 4, lines 64, 66, 68, Col. 5, line 2, Col. 6, lines 31, 35 37, 39, 41, Col. 7, line 46, Col. 8, lines 47, 68 and Col. 9, line 2 | Before "1,8]" insert --[-- |
| Col. 5, line 11 | Before "3(4H)-one" insert -- - -- |
| Col. 5, lines 12-13 | Correct spelling of --naphthyridin-- |
| Col. 6, line 25 | After "[3,4-c" insert --]-- |
| Col. 7, line 8 | Before "4,3-c]" insert --  -[ -- |
| Col. 7, lines 12, 22 | After "[4,3-" insert --c-- |
| Col. 7, line 53 | After "1-isopropyl-6-[" delete "4-(2-" and substitute --2-[4-(2- -- |
| Col. 7, line 56 | Delete "1methyl" and substitute --1-methyl-- |
| Col. 8, line 6 | Delete "8--" and substitute -- 8]- -- |
| Col. 8, line 16 | After "dihydropyrido" insert -- - -- |
| Col. 8, line 67 | Correct --dihydropyrido-- |
| Col. 10, line 43 | Correct --administration-- |
| Col. 13, line 21 | Correct --meaning-- |
| Col. 16, line 2 | Before "-Methyl" insert --1--. |
| Col. 19, line 65 | Before "active" delete "the" and substitute --The-- |
| Col. 20, line 18 | After "group" delete "or," |
| Col. 21, line 16 | After "[1,8" insert --]-- |
| Col. 21, line 20 | After "1,2" insert -- - -- |

UNITED STATES PATENT AND TRADEMARK OFFICE
CERTIFICATE OF CORRECTION

PATENT NO. : 4,801,590

DATED : January 31, 1989

INVENTOR(S) : Erich Cohnen, et al

It is certified that error appears in the above-identified patent and that said Letters Patent is hereby corrected as shown below:

Col. 21, line 20        Before "4,3-c]" insert --[--
Col. 22, line 9         Correct spelling of --prophylaxis--

Signed and Sealed this

Twenty-first Day of November, 1989

Attest:

JEFFREY M. SAMUELS

*Attesting Officer*      *Acting Commissioner of Patents and Trademarks*